United States Patent [19]

Muneyuki et al.

[11] Patent Number: 4,983,391
[45] Date of Patent: Jan. 8, 1991

[54] FABRIC INSECTICIDE

[75] Inventors: Ryonosuke Muneyuki; Hiroyuki Kanamaru, both of Tokyo, Japan

[73] Assignee: S.T. Chemical Co., Ltd., Tokyo, Japan

[21] Appl. No.: 391,043

[22] Filed: Aug. 9, 1989

[51] Int. Cl.$^5$ ............... A01N 25/34; A01N 25/00; A01N 25/08; A01N 47/10
[52] U.S. Cl. ................... 424/408; 424/405; 424/406; 424/409; 514/478
[58] Field of Search ............ 424/408, 405, 406, 409; 514/478

[56] References Cited
U.S. PATENT DOCUMENTS
4,464,390  8/1984  Kochansky et al. ............ 514/478

FOREIGN PATENT DOCUMENTS
52-136919  11/1977  Japan .
63-216808   9/1988  Japan .
931420      7/1961  United Kingdom ............ 514/478

Primary Examiner—Lester L. Lee
Assistant Examiner—Carmen Pili-Curtis

[57] ABSTRACT

An insecticide for protecting a fibrous material from the damage by an insect, which comprises a carbamic ester of the formula:

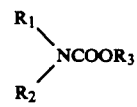

wherein $R_1$ and $R_2$ are, the same or different, each a hydrogen atom or a lower alkyl group and $R_3$ is a lower alkyl group as an active ingredient.

4 Claims, No Drawings

FABRIC INSECTICIDE

The present invention relates to an insecticide for fibrous materials. More specifically, it relates to an insecticide for prevention of fibrous materials such as fabrics and clothes from the damage by insects such as beetles, moths and worms.

Hitherto, there are known naphthalene, camphor, p-dichlorobenzene, etc. as insecticides. However, their lethal activities are not satisfactory. For instance, naphthalene can not prevent the feeding damage of fibrous materials by the larvae of insects, and naphthalene and camphor are weak in lethal activity against the larvae. p-Dichlorobenzene shows higher prevention of feeding damage and stronger lethal activity than naphthalene and camphor but its effect is still not adequate In addition, the combined use of p-dichlorobenzene with camphor produces stains on fibrous materials and gives damage on plastics enveloping such fibrous materials.

As the result of an extensive study overcoming said drawbacks as seen on conventional fabric insecticides, it has been found that a carbamic ester of the formula:

(I)

wherein $R_1$ and $R_2$ are, the same or different, each a hydrogen atom or a lower alkyl group (e.g. methyl, ethyl) and $R_3$ is a lower alkyl group (e.g. methyl, ethyl, n-propyl, isopropyl, n-butyl, isobutyl, sec-butyl) shows a remarkable insecticidal effect and produces significant prevention of the feeding damage by insects or their larvae. This invention is based on the above finding.

Typical examples of the carbamic ester (I) are as follows:

| Chemical formula | M.P. | $LD_{50}$ (mouse) |
|---|---|---|
| $H_2NCOOCH_3$ | 56–58° C. | 5,000 mg/kg (oral) |
| $H_2NCOOC_2H_5$ | 49–51° C. | 2,500 mg/kg (oral) |
| $H_2NCOOCH_2CH_2CH_3$ | 53° C. | — |
| $H_2NCOO(CH_2)_3CH_3$ | 51–53° C. | 540 mg/kg (subcutaneous) |
| $H_2NCOOC(CH_3)_3$ | 105–108° C. | — |
| $CH_3NHCOOC_2H_5$ | (B.P., 170° C.) | — |
| $(CH_3)_2NCOOC_2H_5$ | — | 1050 mg/kg (subcutaneous) |

A typical test example which supports the excellent insecticidal activity of the carbamic ester (I) is set forth below.

A weighed amount (1 g) of each test compound was placed at the bottom of a glass bottle (inner volume, 1 liter) having a cap. Ten larvae of clothes moth (*Tinea pellionella*) and a lump of wool (about 100 mg) were admitted into a stainless wire cage (volume, about 0.08 liter), which was then admitted into the glass bottle. The glass bottle was allowed to stand in a bath of constant temperature and humidity (20° C.; 75 % R.H), and observation was made one week and one month thereafter. The averaged results obtained with five experiments carried out at the same time are shown in Table 1.

TABLE 1

| | After one week | | After one month | |
|---|---|---|---|---|
| Test compound | Damaged weight of wool (mg) | Number of killed larvae | Damaged weight of wool (mg) | Number of killed larvae |
| Methyl carbamate | 0 | 8/10 | 0 | 10/10 |
| t-Butyl carbamate | 26 | 2/10 | 52 | 4/10 |
| Ethyl N-methyl-carbamate | 0 | 10/10 | 0 | 10/10 |
| None | 56.7 | 0/10 | 200 | 0/10 |
| p-Dichloro-benzene | 4 | 9/10 | 6 | 10/10 |

Judging from the above test result, the carbamic esters (I) according to the invention may be understood to show a high insecticidal effect. The damaged weight of wool in their presence is quite small. Thus, they are useful as insecticides. Among the carbamic esters (I), particularly preferred is methyl carbamate, because of its remarkable insecticidal potency. Advantageously, it is a crystalline solid at room temperature, can be readily processed in an appropriate shape (e.g. tablets, balls, granules) by itself and is vaporized in the atmosphere. It shows only a very low toxicity to mammals and is colorless and odorless so that it can be used without causing any trouble to mammals and fabric materials.

For the practical use, the carbamic ester (I) of this invention may be applied as such to fibrous materials to be protected from the damage by insects. Alternatively, it may be formulated together with any solid or liquid carrier or diluent (e.g. adamantane, liquid paraffin) into a conventional preparation form (e.g. tablets, balls, granules); the thus formulated preparation is applicable to fibrous materials to be protected. When the carbamic ester (I) is in a solid at room temperature, it is usually processed into an appropriate shape with or without any additive such as a flavoring agent or a fungicide, and the shaped product is kept together with a fabric material in a state that a vapor of the carbamic ester (I) produced from the shaped product under the atmospheric condition is contacted with the fabric material so as to exert the preventive effect from the damage by an insect. When any additive is incorporated into the carbamic ester (I), its content may be from about 0.01 to 0.1% by weight based on the weight of the shaped product In case of the shaped product being in a weight of about 5 grams, its vaporization in the atmosphere at room temperature will be usually perfected within about 10 days, although this period is greatly varied with the kind of the carbamic ester (I), the size and form of the shaped product and the circumstances under which the shaped product is present. In general, the size and form of the shaped product may be appropriately decided so that the shaped product is vaporized in about 1 to 3 months to disappear. For the control of the vaporization period, the shaped product is usually accommodated in a container such as a bag having an appropriate air-permeability.

A practical embodiment of the invention is illustratively shown in the following Example.

EXAMPLE 1

Methyl carbamate was tabletted by a conventional procedure to make tablets, which had each a weight of 1 g and were lapped with partial air-tight paper. The tablets thus obtained were placed on a fabric made of wool (about 2 kg) in a container (50 liters) made of wood. After one month, the tablet decreased to ¼ time and no damage from the larvae set aside was observed on the fabric.

The insecticide of the invention is advantageous in exerting a high insecticidal effect with less toxicity to human beings.

What is claimed is:

1. An insecticide in a solid form to be used by vaporization to prevent damage to a fibrous material caused by an insect harmful to fibrous materials, which comprises as an active ingredient at least one carbamic ester selected from the group consisting of methyl carbamate and ethyl N-methylcarbamate.

2. The insecticide according to claim 1, wherein the carbamic ester is methyl carbamate.

3. An insecticide according to claim 2, which is in a tablet form.

4. An insecticide according to claim 1, which is in a tablet form.

* * * * *